United States Patent
Ishimoto et al.

(10) Patent No.: US 8,658,339 B2
(45) Date of Patent: Feb. 25, 2014

(54) NEGATIVE CHARGE CONTROLLING AGENT AND STATIC CHARGE IMAGE DEVELOPING TONER USING THE SAME, AND METHOD FOR PRODUCING THE SAME

(75) Inventors: Takayuki Ishimoto, Saitama (JP); Yutaka Kukimoto, Tokyo (JP); Shinji Yatabe, Oura-gun (JP)

(73) Assignee: Fujikura Kasei Co., Ltd., Tokyo (JP)

( * ) Notice: Subject to any disclaimer, the term of this patent is extended or adjusted under 35 U.S.C. 154(b) by 2256 days.

(21) Appl. No.: 10/542,589

(22) PCT Filed: Jan. 21, 2004

(86) PCT No.: PCT/JP2004/000495
§ 371 (c)(1),
(2), (4) Date: Jul. 19, 2005

(87) PCT Pub. No.: WO2004/066030
PCT Pub. Date: Aug. 5, 2004

(65) Prior Publication Data
US 2006/0083999 A1    Apr. 20, 2006

(30) Foreign Application Priority Data

Jan. 23, 2003    (JP) .................................. 2003-015207

(51) Int. Cl.
*G03G 9/08*    (2006.01)
(52) U.S. Cl.
USPC .................. 430/108.1; 430/106.1; 430/108.6; 430/109.3; 430/123.4
(58) Field of Classification Search
USPC .......... 430/108.1, 106.1, 108.6, 109.3, 123.4; 568/718; 528/129, 153, 155
See application file for complete search history.

(56) References Cited

U.S. PATENT DOCUMENTS

| | | | |
|---|---|---|---|
| 3,851,012 A * | 11/1974 | Wertz | 525/135 |
| 5,023,315 A * | 6/1991 | Ceurvorst | 528/323 |
| 5,714,568 A * | 2/1998 | Nava | 528/196 |
| 5,925,691 A * | 7/1999 | Funada et al. | 523/145 |
| 6,013,724 A * | 1/2000 | Mizutani et al. | 524/588 |
| 6,437,080 B1 * | 8/2002 | McGrail et al. | 528/171 |
| 6,534,231 B1 | 3/2003 | Yamanaka et al. | 430/108.3 |
| 2003/0022109 A1 * | 1/2003 | Kobayashi | 430/311 |
| 2003/0104298 A1 | 6/2003 | Yamanaka et al. | 430/108.3 |
| 2003/0232185 A1 * | 12/2003 | Shimamura et al. | 428/323 |
| 2004/0175643 A1 * | 9/2004 | Baba et al. | 430/109.4 |

FOREIGN PATENT DOCUMENTS

| | | | |
|---|---|---|---|
| EP | 0606149 A2 | | 7/1994 |
| EP | 0875793 A2 | | 11/1998 |
| JP | 41-20153 | | 11/1966 |
| JP | 43-27596 | | 11/1968 |
| JP | 63-266462 | | 11/1988 |
| JP | 03255119 A | * | 11/1991 |
| JP | 4139456 | | 5/1992 |
| JP | 10104881 | | 4/1998 |
| JP | 10104881 A | * | 4/1998 |
| JP | 10228134 | | 8/1998 |
| JP | 11311879 | | 11/1999 |
| JP | 2000162825 | | 6/2000 |
| WO | WO0167180 | * | 9/2001 |

OTHER PUBLICATIONS

Machine translation of Japanese patent 10-104881.*
G.S. Learmonth and D.P. Searle, University of Aston in Birmingham, England, Thermal Degradation of Phenolic Resins. V, Journal of APplied Polymer Science, vol. 13, pp. 437-443, 1969.*
International Search Report dated Jul. 6, 2004 in Japanese and English, 4 pages.
Japanese Office Action (untranslated) (2 pages).
Edmund Walker for Mewburn Ellis LLP, Letter to Shiga International Patent Office, Apr. 2, 2008, pp. 1-2.
European Patent Office, Supplementary European Search Report, Apr. 1, 2008, pp, 1-3.

* cited by examiner

*Primary Examiner* — Mark F Huff
*Assistant Examiner* — Rachel Zhang
(74) *Attorney, Agent, or Firm* — Wood, Herron & Evans, LLP

(57) ABSTRACT

A negative charge controlling agent, wherein: the negative charge controlling agent comprises polycondensation product obtained by a polycondensation reaction of phenols and aldehydes; and the phenols comprises a (A) mononucleus phenolic compound which has one phenolic hydroxy group in which a hydrogen is bonded at the ortho position of a hydroxyl group of the phenolic hydroxy group and a (B) multinucleus phenolic compound which has at least two phenolic hydroxy groups in which a hydrogen is bonded at the ortho position of a hydroxyl group of each of the phenolic hydroxy group; and the content of the (B) phenolic compound in the phenols is 1 to 30 mol %.

3 Claims, No Drawings

NEGATIVE CHARGE CONTROLLING AGENT AND STATIC CHARGE IMAGE DEVELOPING TONER USING THE SAME, AND METHOD FOR PRODUCING THE SAME

TECHNICAL FIELD

The present invention relates to a toner for developing electrostatic charge image, a negative charge controlling agent which is used for the toner, and a manufacturing method of the negative charge controlling agent. Priority is claimed on Japanese Patent Application No. 2003-015207, the content of which is incorporated herein by reference.

BACKGROUND ART

In addition to the wet type toner, a dry type toner has been widely used for a developer developing for an electrostatic latent image. When the electrostatic latent image is developed with the dry type toner, toner particles thereof are required to have positive or negative charge according to polarity of the electrostatic latent image to be developed. Accordingly, various kinds of charge controlling agents are studied in order to control charging ability of the toner particles.

For example, a phenol type compound is disclosed in Japanese Unexamined Patent Application, First Publication, No. 63-266462, and a negative charge controlling agent which consists of a chromium containing azo dye is disclosed in Japanese Examined Patent Application, Second Publication, No. 41-20153 and Japanese Examined Patent Publication, Second Publication, No. 43-27596 and the like.

However, although the phenol type compound disclosed in the Japanese Unexamined Patent Application, First Publication, No. 63-266462 provides a certain amount of negative charging ability, the level of the charging amount was insufficient. Furthermore, since the color of the chromium containing azo dye disclosed in the Japanese Examined Patent Publication, Second Publication, No. 41-20153, the Japanese Examined Patent Publication, Second Publication, No. 43-27596 and the like is black, the azo dye provides a bad influence on the hue of a color toner when it is used for the toner. Moreover, the azo dye provides bad influence on the environment, since the azo dye includes chromium.

The present invention was achieved based on the aforementioned circumstances. An object of the present invention is to provide: a negative charge controlling agent, wherein the charge controlling agent can provide sufficient charging ability, and has good electrostatic charge rising property, has good compatibility with a binder resin, and has good dispersibility, and by which hue of toner is not influenced if the charge controlling agent is used in the color toner, and a bad influence is not applied on the environment; and a toner for developing an electrostatic charge image by which a clear image can be obtained.

DISCLOSURE OF INVENTION

A negative charge controlling agent of the present invention is a negative charge controlling agent, wherein the negative charge controlling agent comprises polycondensation product obtained by a polycondensation reaction of phenols and aldehydes; and the phenols comprise a (A) mononucleus phenolic compound which has one phenolic hydroxy group in which a hydrogen is bonded at the ortho position of a hydroxy group of the phenolic hydroxy group and a (B) multinucleus phenolic compound which has at least two phenolic hydroxy groups in which a hydrogen is bonded at the ortho position of a hydroxyl group of each of the phenolic hydroxy group; and the content of the (B) phenolic compound in the phenols is 1 to 30 mol %.

A toner for developing electrostatic charge image of the present invention is a toner which comprises 0.1 to 10 parts by mass of a negative charge controlling agent per 100 parts by mass of a binder resin; and the negative charge controlling agent comprises polycondensation product obtained by polycondensation reaction of phenols and aldehydes; and the phenols comprise a (A) mononucleus phenolic compound which has one phenolic hydroxy group in which a hydrogen is bonded at the ortho position of a hydroxy group of the phenolic hydroxy group; and a (B) multinucleus phenolic compound which has at least two phenolic hydroxy groups in which a hydrogen is bonded at the ortho position of each of the phenolic hydroxy group; and the content of the (B) phenolic compound in the phenols is 1 to 30 mol %.

A manufacturing method of a negative charge controlling agent of the present invention comprises:
preparing a (A) mononucleus phenolic compound, which has one phenolic hydroxy group in which a hydrogen is bonded at the ortho position of a hydroxy group of the phenolic hydroxy group, and a (B) multinucleus phenolic compound, which has at least two phenolic hydroxy groups in which a hydrogen is bonded at the ortho position of a hydroxyl group of each of the phenolic hydroxy group, to provide phenols comprising, the (A) mononucleus phenolic compound and the (B) multinucleus phenolic compound wherein the content of the (B) phenolic compound in the phenols is 1 to 30 mol %; and conducting a polycondensation reaction between the phenols and aldehydes to obtain a polycondensation product.

BEST MODE FOR CARRYING OUT THE INVENTION

Hereinafter, the present invention will be described below in detail. The present invention relates to a toner for developing an electrostatic charge image, wherein the toner is used for electrophotography, electrostatic recording, and electrostatic printing, and relates to a negative charge controlling agent used for the toner. The negative charge controlling agent of the present invention comprises a polycondensation product obtained by a polycondensation reaction between phenols and aldehydes. As the phenols, a (A) mononucleus phenolic compound, which has one phenolic hydroxy group in which a hydrogen is bonded at the ortho position of the hydroxy group (hereinafter, it may be described simply as a mononucleus phenolic compound), and a (B) multinucleus phenolic compound, which has at least two phenolic hydroxy groups in which a hydrogen is bonded at the ortho position of each of the hydroxy group (hereinafter, it may be described simply as a multinucleus phenolic compound), are used in combination.

Here, the recitation "a hydrogen is bonded at the ortho position of the hydroxyl group" means that both carbons, which are adjacent to a carbon bonds to the hydroxyl group, are bonding only to hydrogen groups except that the both carbons are bonding to carbons which constitute an aromatic ring.

Moreover, two or more kinds of the (A) mononucleus phenolic compound and/or the (B) multinucleus phenolic compound may be comprised each independently in the phenols.

Examples of the (A) mononucleus phenolic compound include p-alkyl phenol, p-aralkyl phenol, p-phenyl phenol, and p-hydroxy benzoic acid ester. These compounds may be used singly and be used by mixing two or more kinds thereof.

The (A) mononucleus phenolic compound is described below.

As the (A) mononucleus phenolic compound, a compound represented by a following general formula (1) is examined.

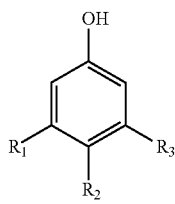

(1)

In the general formula (1), $R_1$ and $R_3$ each independently represents a hydrogen, a halogen, an alkyl group, an aralkyl group, a substituted or non-substituted amino group. Preferable examples of the alkyl group include alkyl groups having 1 to 12 carbons, such as a methyl group, an ethyl group, a butyl group, an octyl group, and a dodecyl group. Examples of the aralkyl group include a benzyl group and cumyl group, and examples of the substituted amino group include —$N(CH_3)_2$, —$N(C_2H_5)_2$, and —$N(C_3H_7)_2$.

In the general formula (1), $R_2$ represents a hydrogen, a halogen, an alkyl group, —$COC_mH_{2m+1}$ (m is an integer of 1 to 20), an aralkyl group, a substituted or a non-substituted phenyl group, a substituted or non-substituted amino group, a nitro group, an alicyclic group, —$SO_3H$, —$Si(CH_3)_3$, an alkoxyl group, a carboxyl group, a sulfonamide group, a carbamoyl group, a cyano group, a carboxylate group, or an acyl group. Those groups exampled as $R_1$ and $R_3$ can also be cited as examples of the alkyl group and the aralkyl group of $R_2$, and alkyl groups having 1 to 12 carbon atoms which may be branched and also as $R_1$ and $R_3$ can be cited as examples of a substituent of the substited amino group of $R_2$. Examples of the substituted phenyl group include those groups wherein at least one of hydrogen of the phenyl group is substituted with an alkyl group having 1 to 8 carbon atoms, a halogen, a carboxyl group, a hydroxyl group, a cyano group, a nitro group, a halogenated methyl group, a trimethylsilyl group, an amide group having 1 to 8 carbon atoms, an acyl group having 1 to 12 carbon atoms, a sulfonyl group having 1 to 12 carbon atoms, and an ether group having 1 to 12 carbon atoms. Examples of the alicyclic group include a cyclohexyl group and a cyclopentyl group. Examples of the alkoxyl group include the groups having 1 to 12 carbon atoms, and examples of the carboxylate group which can be shown by —$COOR_{35}$ include the groups wherein $R_{35}$ may be an alkyl group having 1 to 18 carbon atoms which may be branched, a substituted or non-substituted phenyl group, or a substituted or non-substituted aralkyl group.

Preferable examples of the compound represented by the general formula (1) include a p-t-butyl phenol, a p-t-octyl phenol, a p-(α-cumyl phenol), a p-phenyl phenol, and a 4-hydroxybenzoate. The phenolic compound (A) may be used singly or as a mixture of two or more kinds thereof.

Examples of the multinucleus phenolic compound (B) include bisphenols, biphenol derivatives, bisphenol derivatives, trisphenols and derivatives thereof, tetra-kis phenols, and derivatives thereof.

As the biphenol derivatives, a compound represented by the following general formula (2) can be cited as examples.

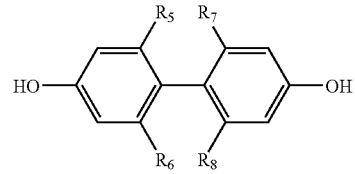

(2)

In the general formula (2), $R_5$ to $R_8$ are each independently represent a hydrogen, an alkyl group, a perfluoro alkyl group, an alicyclic group, an aralkyl group, a substituted or a non-substituted phenyl group, an alkoxyl group, an aryl group, a sulfonamide group, a carbamoyl group, a cyano group, a carboxylate group, an acyl group, a vinyl group, or halogen. Preferable examples of the alkyl group include alkyl groups having 1 to 8 carbon atoms, such as a methyl group, an ethyl group, a propyl group, a butyl group, a pentyl group, a hexyl group, a heptyl group, and an octyl group.

Examples of the bisphenols and bisphenol derivatives include a compound represented by a following general formula (3).

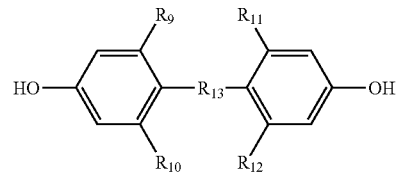

(3)

In the general formula (3), $R_9$ to $R_{12}$ of the formula (3) represent the same contents of $R_5$ to $R_8$ in the formula (2). $R_{13}$ represents —$SO_2$—, —$(CR_{14}R_{15})_n$— (here, n represents the number of 1 to 12, and $R_{14}$ and $R_{15}$ may be different each other; when n represents the number of 2 or more, $R_{14}$ and $R_{15}$ may be different from each other every in repeating unit), —O—, a substituted or non-substituted cyclo ring having 3 to 8 carbon atoms represented by a following general formula (4), or a group represented by a following general formula (5). $R_{14}$ and $R_{15}$ each independently represent a hydrogen, an alkyl group, a perfluoro alkyl group, a substituted or non-substituted phenyl group. Examples of the alkyl group include alkyl groups having 1 to 16 carbon atoms, and those groups may be branched or not be branched. Examples of the perfluoro alkyl group include groups having 1 to 16 carbon atoms, and those groups may be branched. Examples of the substituted phenyl group include a phenyl group, wherein one or more hydrogen of the phenyl group is substituted by a group such as an alkyl group having 1 to 8 carbon atoms, a halogen, a carboxyl group, a hydroxy group, a cyano group, a nitro group, a halogenated methyl group, a trimethyl silyl group, an amide group having 1 to 8 carbon atoms, an acyl group having 1 to 12 carbon atoms, a sulfonyl group having 1 to 12 carbon atoms, and an ether group having 1 to 12 carbon atoms.

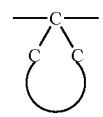

(4)

-continued

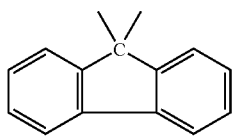
(5)

Examples of the trisphenols and derivatives thereof include a compound represented by a following general formula (6).

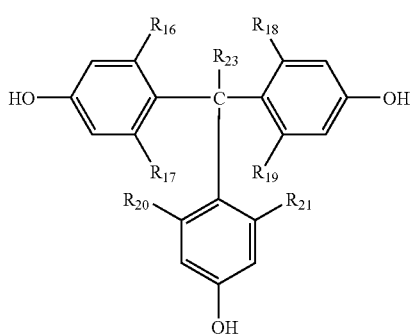
(6)

In the general formula (6), $R_{16}$ to $R_{21}$, represent the same contents of $R_5$ to $R_8$ in the general formula (2), and $R_{23}$ represents the same content of $R_{14}$ and $R_{15}$ in the general formula (3).

Examples of the tetrakis phenols or derivatives thereof include a compound represented by a following general formula (7).

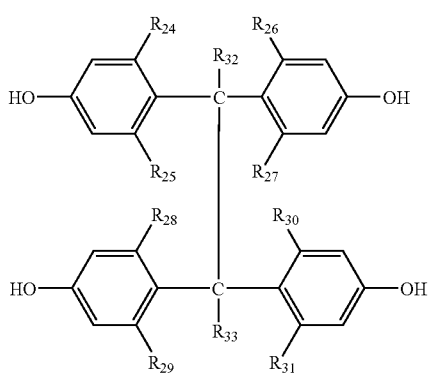
(7)

In the general formula (7), $R_{24}$ to $R_{31}$, represent the same contents of $R_5$ to $R_8$ in the general formula (2), and $R_{32}$ and $R_{33}$ represent the same contents of $R_{14}$ and $R_{15}$ in the general formula (3).

Moreover, the contents of the multinucleus phenolic compound (B) in the phenols are 1 to 30 mol %. It is preferably 2 to 20 mol %, and more preferably 4 to 15 mol %. If the molar content of the multinucleus phenolic compound (B) is less than 1 mol % or exceeds 30 mol %, sufficient negative charging ability may not be obtained, and especially when it exceeds 30 mol %, there is a tendency that the dispersibility of the compound into a binder resin becomes poor. The multinucleus phenolic compound (B) can be used as one kind or two or more kinds thereof.

Examples of the aldehydes include an aldehyde such as a paraformaldehyde, a formaldehyde, and a paraldehyd, and an aldehyde such as a furfural represented by a following general formula (8).

$$R_{34}CHO \qquad (8)$$

In the general formula (8), $R_{34}$ represents an alkyl group, a substituted or non-substituted phenyl group, or a heterocyclic group (for example, a furyl group, a pyridyl group, and the like) which contains a nitrogen atom or an oxygen atom. The alkyl group may be branched or not be branched, and examples thereof include alkyl groups having 1 to 12 carbon atoms such as a methyl group, an ethyl group, a butyl group, an octyl group, and a dodecyl group. Examples of the substituted phenyl group include phenyl groups wherein one or more of hydrogen of a phenyl group is substituted with an alkyl group having 1 to 8 carbon atoms, a halogen, a carboxyl group, a hydroxy group, a cyano group, a nitro group, a halogenated methyl group, a trimethyl silyl group, an amide group having 1 to 8 carbon atoms, an acyl group having 1 to 12 carbon atoms, a sulfonyl group having 1 to 12 carbon atoms, and an ether group having 1 to 12 carbon atoms. The aldehydes may be used as one kind or two or more kinds thereof. Moreover, it is preferable that the aforementioned aldehydes be a paraformaldehyde and/or a formaldehyde.

The polycondensated product obtained by the polycondensation reaction of the phenols and the aldehydes explained above is used as a negative charge controlling agent.

Examples of a method of the reaction include: a method wherein phenols and aldehydes are added in an organic solvent such as a xylene, and they are allowed to undergo a polycondensation reaction for three to twenty hours while water therein is distilled off at a temperature of 80° C. to a boiling point of the organic solvent, preferably at a temperature of 100° C. to a boiling point of the organic solvent, in the presence of a strong base such as a hydroxide of an alkali metal or an alkaline earth metal, and then a recrystallization is conducted using poor solvents such as an alcohol; and a method wherein, after the aforementioned polycondensation reaction, a drying under reduced pressure is conducted for removing the organic solvent followed by a washing which is conducted with alcohols such as methanol, ethanol and isopropanol.

As the strong base, sodium hydroxide, rubidium hydroxide, potassium hydroxide, and the like can be used preferably.

There is no particular limitation with respect to a ratio between the mass of the organic solvent used and the mass of the phenols and the aldehydes. It is preferable that an organic solvent be used in a range of 0.5 to 100 times as compared to the totals of the phenols and the aldehydes, and more preferably it be used in a range of 1 to 10 times. Moreover, the molar ratio of the phenol to the aldehyde is 1:0.5 to 5, and it is prefereably 1:1 to 2.

Here, the molar ratio of the phenols to the strong base which can be used in the reaction is not particularly limited. The ratio of the phenols to the strong base is 1:10 to 0.00001, and it is preferably 1:0.01 to 0.001.

A reaction of a phenolic compound and an aldehyde compound in the presence of a strong bases such as a hydroxide of an alkali metal or an alkaline earth metal is described such that the aldehyde conducts the nucleophilic substitution reaction at the ortho-position or the para-position with respect to a hydroxyl group of the phenolic compound, and a condensation reaction is repeated, in the "Organic Chemistry Handbook" (published by Gihoudou on Jul. 10, 1968 (Showa 43); recitation from page 532), and "Rikagaku Jiten" (Iwanami Phisical and Chemical Dictionary, published by Iwanami Shoten, fifth edition, pp. 198-199). Therefore, when multi-nucleus phenols are used as the phenolic compound, molecular weight of the reaction product increases, because the number of reactive sites to the aldehyde increases. As a result, a molecular weight distribution of the reaction product becomes wide, and entanglement degree between the reaction product and the molecule of the binder resin become large. Then, a distributed state of the reaction product becomes more uniform, and high charging ability can be applied to a toner if the multinucleus phenols is added thereto.

When a polycondensation product obtained as described above is evaluated with gel permeation chromatography, a mass average molecular weight is 1700 or more, and a dispersion degree which shows a molecular weight distribution, that is, a mass average molecular weight/a number average molecular weight, is 1.2 to 20 in general.

The mass average molecular weight thereof is preferably 2000 or more and 10000 or less, and more preferably 2000 or more and 5000 or less. The dispersion degree is preferably 1.2 to 10, and more preferably 1.2 to 5. If the mass average molecule weight is less than 1700, sufficient charge may not be obtained. Furthermore, if the dispersion degree is less than 1.2, sufficient charge may not be obtained, and if the dispersion degree exceeds 20, dispersing ability to the binder resin deteriorates, and also sufficient charge may not be obtained.

The polycondensation product obtained as described above can be used as a negative charge controlling agent after drying. Furthermore, it is preferable that the obtained polycondensation product be repeatedly recrystallized or washed with alcohols such as methanol to remove a methanol soluble component therefrom. Accordingly, it is preferable that the polycondensation product of the present invention be not soluble into alcohol such as methanol at an ordinary temperature. The negative charge controlling agent obtained after drying has a pale white or pale yellow color, and therefore, even if it is used for a color toner, it does not affect that hue of the toner. Furthermore, as described below, compatibility and dispersibility between the agent and a binder resin is good when the agent is added to the binder resin.

A toner which is excellent in charging property and charge rising ability can be obtained by using the thus obtained negative charge controlling agent in an amount of 0.1 to 10 parts by mass, more preferably 1 to 7 parts by mass, based on 100 parts by mass of the binder resin, and producing a toner which has a particle size diameter of 5 to 15 μm, and preferably of 5 to 10 μm. Here, if the mixing amount of the negative charge controlling agent is less than 0.1 part by mass, charging ability and charge rising ability of the toner may be insufficient, and on the other hand, if the mixing amount of the negative charge controlling agent exceeds 10 parts by mass, the fixing property of the toner may be deteriorated.

Examples of the binder resin used for the toner include: homopolymer of styrene and substituted styrene such as polystyrene, poly-p-chlorostyrene, and polyvinyl toluene; styrene based copolymers such as styrene-p-chlorostyrene copolymer, styrene-vinyl toluene copolymer, styrene-vinylnaphthalene copolymer, styrene-acrylate copolymer, styrene-methylacrylate copolymer, styrene-α-chloromethylmethacrylate copolymer, styrene-acrylonitrile copolymer, styrene-vinylmethylether copolymer, styrene-vinylether copolymer, styrene-vinylmethylketone copolymer, styrene-butadiene copolymer, styrene-isoprene copolymer, styrene-acrylonitrile-indene copolymer; polyvinyl chloride; phenol resin; natural modified phenol resin; maleic acid resin of modified natural resin; acrylic resin; methacrylic resin; polyvinyl acetate; silicone resin; polyester resin; polyurethane; polyamide resin; furan resin; epoxy resin; xylene resin; polyvinylbutyral resin; terpene resin; coumarone-indene resin; and petroleum type resin.

Cross-linked resins can also be used. A compound having two or more polymerizable double bonds can be mainly used as a crosslinking agent singly or as a mixture of the compound. Examples thereof include: aromatic divinyl compounds such as divinylbenzene, and divinylnaphthalene; carboxylates having two double bonds such as ethylene glycol diacrylate, ethylene glycol dimethacrylate, 1,3-butanediol dimethacrylate; divinyl compounds such as divinyl aniline, divinyl ether, divinyl sulfide, and divinyl sulfone; and compounds having three or more vinyl groups.

Moreover, when a toner is used for a pressure-fixing method, it is desirable that binder resin such as polyethylene, polypropylene, polymethylene, polyurethane elastomer, ethylene-ethyl acrylate copolymer, ethylene-vinyl acetate copolymer, an ionomer resin, a styrene-butadiene copolymer, a styrene-isoprene copolymer, linear saturated polyester, and paraffin, be used as a binder resin for the toner.

A colorant is properly contained in the toner if necessary. There is no restriction of the colorant in particular. Examples of the colorant include carbon black, lamp black, black iron oxide, ultramarine, nigrosine dye, Aniline blue, Phthalocyanine blue, Phthalocyanine green, Hansa Yellow G, Rhodamine 6G, Calco Oil Blue, chrome yellow, quinacridone, benzidine yellow, rose bengal, triaryl methane based dye, monoazo type and diazo type dyes and pigments. The colorants can be used singly or as a mixture thereof.

Furthermore, an additive may be contained in the toner if needed. Examples of the additives include: a lubricant such as zinc stearate; an abrasive such as cerium oxide and silicon carbide; flowability providing agent such as aluminium oxide; a caking inhibitor; and charging ability providing agent such as carbon black, and tin oxide.

Fluorine containing polymer fine particles such as fine particles of polyvinylidene fluoride may be used for the toner in order to improve flowability, polishing ability, and charging stability of the toner. Moreover, in order to improve releasing ability of the toner at the time of heat roll fixing, the toner may include about 0.5 to 5% by mass of a wax-like substance such as a low molecular weight polyethylene, a low molecular weight polypropylene, a microcrystalline wax, a carnauba wax, a xazole wax, and a paraffin wax. Furthermore, a magnetic material may be suitably added to the toner if needed to obtain a magnetic toner. Examples of the magnetic material include: iron oxide such as magnetite, γ-iron oxide, ferrite, and iron excess type ferrite; metal such as iron, cobalt and nickel; alloy and mixture of the metal such as iron, cobalt and nickel and metal such as an aluminum, cobalt, copper, lead, magnesium, tin, zinc, antimony, beryllium, bismuth, cadmium, calcium, manganese, selenium, titanium, tungsten, and vanadium.

As the manufacturing method for the toner, there is no restriction in particular. Examples of the method are described below.

Examples thereof include: a method wherein a negative charge controlling agent, a binder resin, a colorant, various additives which may be added if required and the like are fully mixed in a mixer such as a ball mill, and then sufficient kneading of the mixture is conducted with a kneading machine such as a heat roll kneader and extruder followed by cooling solidification, and then toner is obtained by mechanical grinding and classification of the solidified mixture; a method wherein a negative charge controlling agent, a colorant, various additives which may be added if needed and the like are dispersed in a solution of binder resin, and then spray drying is conducted to obtain toner; a method wherein particles containing a binder resin and a colorant are manufactured, and a negative charge controlling agent is fixed on the surface of the particles; a method wherein a predetermined material is comprised in at least one of core material and shell material to form a micro toner; and a method wherein a negative charge controlling agent, a colorant, and various additives which may be added if needed are mixed with a monomer which form a binder resin to form an emulsion suspension, and then polymerization is conducted to form a toner.

The toner manufactured as described above can be used as it is to develop an electrostatic latent image in a method such as electrophotography, electrostatic recording, or electrostatic printing. Furthermore, the toner can be used in combination with a carrier. As the carrier, a well-known carrier can be used. Examples thereof include magnetic particles such as iron powder, ferrite powder, nickel powder and the like; glass beads; and carrier wherein the surface of the particles and bead is treated with resin and the like. Examples of the resin used for coating a carrier surface include a styrene-acrylate copolymer, a styrene-methacrylate copolymer, an acrylate copolymer, a methacrylate copolymer, a silicone resin, a fluorine containing resin, a polyamide resin, an ionomer resin, and polyphenylene sulfide resin, and the resin may be used singly or as a mixture thereof.

The negative charge controlling agent explained above include polycondensed material wherein it is obtained by a condensation polymerization between aldehydes and phenols in which a specific mononucleus phenol compound (A) and a specific multinucleus phenol compound (B) are used together in a specific ratio. Therefore charge rising ability of the agent is good, and the agent can provide sufficient charging ability to the toner, and compatibility between the agent and a binder resin is good, and dispersibility of the agent to the binder resin is also good. Furthermore, such a product can be manufactured safely. Moreover, since color of the negative charge controlling agent is pale white or pale yellow, hue of toner is not influenced if the negative charge controlling agent is used for a color toner. Furthermore, the product is excellent in environmental point, since it does not comprise elements such as chrome.

EXAMPLE

Hereafter, the present invention is explained concretely by showing examples. In addition, "parts" in examples means "parts by mass".

Example 1

0.45 mole of p-t-butyl phenol, 0.032 mole of 2,2'-bis(4-hydroxy phenyl)propane, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product.

Degree of dispersion (a mass average molecular weight/a number average molecular weight) of the obtained product and the like are shown in Table 1. Values of a mass average molecular weight and a number average molecular weight were determined by gel permeation chromatography. Shodex RI-71 (manufactured by Showa Denko K. K.) was used as detector, and TSKgel G3000Hxl and TSKgel G2000Hxl and G1MHhr-M (manufactured by Tosoh Corporation) were used as a column in the measurement.

Subsequently, black toner was manufactured and evaluated using the obtained product by the methods according to following (a) toner manufacturing method and blow off charge performance evaluation method. Evaluation results are shown in Table 1.

(a) Toner Manufacturing Method and Blow Off Charge Performance Evaluation Method 1 part of the product obtained in the example as a negative charge controlling agent, 100 parts of styrene-acrylic copolymer as a binder resin, 5 parts of carbon black (MA #100, manufactured by Mitsubishi Chemical Co., Ltd.) as a colorant, 4 parts of Viscol 550P (registered trademark, manufactured by Sanyo Chemical Industries, Ltd.) were melt-mixed with a Labo Plasto mill (manufactured by Toyo Seiki Seisaku-sho, Ltd.). Subsequently, the mixture was ground using a Jet Mill, and then it was classified to obtained a toner having a particle diameter of 5 to 15 μm.

The toner obtained and a carrier (F-150, manufactured by Powder Tech Corporation) were mixed in the ratio of 3:100. After a friction charge of the mixed toner and carrier was conducted for a predetermined time (5 minutes, one hour, or two hours) under the condition of 20° C. and 65% RH, the blow off charge measurement was carried out using a blow-off powder charge measuring instrument TB-203 (manufactured from, Toshiba Chemical Co., Ltd.).

Rising rate is determined as a ratio of charge amount after 5 minutes to charge amount after one hour as shown below.

$$\text{Rising ratio (\%)}=(\text{a charge amount after 5 minutes/a charge amount after one hour})\times 100$$

Example 2

Except that the amounts of p-t-butyl phenol and 2,2'-bis(4-hydroxy phenyl)propane were changed as shown in Table 1, a product was obtained similar to Example 1, and a degree of dispersion (a mass average molecular weight/a number average molecular weight) of the obtained product was determined similar to the Example 1.

Subsequently, a blue toner was manufactured using the obtained product and was evaluated in accordance with a following (b) toner manufacturing method and blow off charge performance evaluation method.

Evaluation results are shown in Table 1.

(b) Toner Manufacturing Method and Blow Off Charge Performance Evaluation Method 1 part of the product obtained in the example as a negative charge controlling agent, 100 parts of styrene-acrylic copolymer as a binder resin, 5 parts of a copper phthalocyanine based oil soluble dye Spilion Blue 2BNH (manufactured by Hodogaya Chemical Co., Ltd.) as a colorant were melt-mixed with a Labo Plasto mill (manufactured by Toyo Seiki Seisaku-sho, Ltd.). Subsequently, the mixture was ground using a Jet Mill, and then it was classified to obtained a toner having a particle diameter of 5 to 15 μm.

The charge measurement was carried out similar to the aforementioned method (a).

Example 3

0.45 mole of p-t-butyl phenol, 0.032 mole of 2,2'-bis(4-hydroxy phenyl)propane, 12.3 g of paraformaldehyde (0.4 mole as formaldehyde), 0.2 mole of furfural, and 3 g of 5N aqueous solution of potassium hydroxide were allowed to undergo a reflex reaction for eight hours in 300 ml of xylene, while water is deleted by distillation. Recrystallization of the reaction solution was conducted using methanol followed by filtration, and filtrated material was further cleaned with methanol, and drying of the obtained solid was conducted to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 2.

Example 4

0.225 mole of p-t-butyl phenol, 0.225 mole of p-t-octyl phenol, 0.032 mole of 2,2'-bis(4-hydroxy phenyl)propane, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 3.

Example 5

0.34 mole of p-t-butyl phenol, 0.11 mole of 2-ethylhexyl 4-hydroxy benzoate, 0.032 mol of 2,2'-bis(4-hydroxy phenyl) propane, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product. Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 4.

Example 6

0.34 mole of p-t-butyl phenol, 0.11 mole of 2-ethylhexyl 4-hydroxy benzoate, 0.032 mole of 4,4'-(1-phenylethylidene) bisphenol, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtrated material was further cleaned with methanol, and drying of the obtained solid was conducted to obtain a product.

Then, degree of dispersion (a mass average molecular weight/a number average molecular weight) of the obtained product was determined in a manner similar to that of the Example 1.

Subsequently, a black toner was manufactured using the obtained product and was evaluated in accordance with the aforementioned (a) toner manufacturing method and blow off charge performance evaluation method. Evaluation results are shown in Table 6.

Example 7

0.45 mole of p-t-butyl phenol, 0.032 mole of 1,1'-bis(4-hydroxy phenyl)cyclohexane, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 5.

Example 8

0.45 mole of p-t-butyl phenol, 0.030 mole of 2,2'-bis(4-hydroxy phenyl)propane, 0.005 mole of 4-4'-4"-ethylidene trisphenol, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product. Then, degree of dispersion (a mass average molecular weight/a number average molecular weight) of the obtained product was determined in a manner similar to that of the Example 1.

Subsequently, a black toner was manufactured using the obtained product and was evaluated in accordance with the aforementioned (a) toner manufacturing method and blow off charge performance evaluation method. Evaluation results are shown in Table 7.

Example 9

0.45 mole of p-t-butyl phenol, 0.032 mol of biphenol, 18.5 g of paraformaldehyde (0.6 mol as formaldehyde), and 3 g of 5N aqueous solution of potassium hydroxide were allowed to undergo a reflux reaction for eight hours in 300 ml of xylene while water is removed by distillation. Drying under reduced pressure of the reaction solution was conducted at 150° C., and a product was obtained after cleaning with methanol.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 8.

Example 10

A black toner was manufactured using the product obtained in the Example 1 and was evaluated in accordance with a following (c) toner manufacturing method and blow off charge performance evaluation method. Evaluation results are shown in Table 9.

(c) Toner Manufacturing Method and Blow Off Charge Performance Evaluation Method 1 part of the product obtained in Example as a negative charge controlling agent, 100 parts of polyester resin (acid value is 10 mgKOH/g, hydroxyl value is 15 mgKOH/g) as a binder resin, 5 parts of a carbon black (MA#100, manufactured by Mitsubishi Chemical Co., Ltd.) as a colorant, and 4 part of Viscol 550P (registered trademark, manufactured by Sanyo Chemical Industries, Ltd.) were melt-mixed with a Labo Plasto mill (manufactured by Toyo Seiki Seisaku-sho, Ltd.). Subsequently, the mixture was ground using a Jet Mill, and then it was classified to obtained a toner having a particle diameter of 5 to 15 μm.

The charge measurement was carried out in a manner similar to that of the aforementioned (a) method.

Example 11

0.35 mole of p-t-butyl phenol, 0.1 mole of p-phenyl phenol, 0.032 mole of 2,2'-bis(4-hydroxy phenyl)propane, 12.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 10.

Example 12

0.35 mole of p-t-butyl phenol, 0.1 mole of p-(α-cumylphenol), 0.032 mole of 2,2'-bis(4-hydroxy phenyl)propane, 12.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. Recrystallization of the reaction solution was conducted using methanol followed by filtration, and filtrated material was further cleaned with methanol, and drying of the obtained solid was conducted to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 11.

Example 13

A toner was manufactured using the product obtained in Example 2 in accordance with a following (d) toner manufacturing method. The obtained toner has white color.

(d) Toner Manufacturing Method 1 part of the product obtained in example as an negative charge controlling agent and 100 parts of styrene-acrylic copolymer as a binder resin were melt-mixed with a Labo Plasto mill (manufactured by Toyo Seiki Seisaku-sho, Ltd.). Subsequently, the mixture was grinded using a Jet Mill, and then, it was classified to obtained a toner having a particle diameter of 5 to 15 μm.

Comparative Example 1

0.45 mole of p-t-butyl phenol, 0.0032 mole of biphenol, 18.5 g of paraformaldehyde (0.6 mole as formaldehyde), and 3 g of 5N aqueous solution of potassium hydroxide were allowed to undergo a reflux reaction for eight hours in 300 ml of xylene, while water is removed by distillation. The reaction solution was dried under reduced pressure at a temperature of 150° C., and an obtained solid was cleaned with methanol to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 8.

Comparative Example 2

0.23 mole of p-t-butyl phenol, 0.11 mole of biphenol, 18.5 g of paraformaldehyde (0.6 mole as formaldehyde), and 3 g of 5N aqueous solution of potassium hydroxide were allowed to undergo a reaction using them in 300 ml of xylene, while water was removed by distillation. However, handling efficiency was deteriorated since large solids were generated, and the reaction had to be stopped.

Comparative Example 3

0.23 mole of p-t-butyl phenol, 0.11 mole of biphenol, 18.5 g of paraformaldehyde (0.6 mole as formaldehyde), and 3 g of 5N aqueous solution of potassium hydroxide were allowed to undergo a reflux reaction in 300 ml of dimethyl formaldehyde, while solvent was removed and new solvent was added to compensate for lost solvent. The reaction solution was dried under reduced pressure at a temperature of 150° C., and an obtained solid was cleaned with methanol to obtain a product.

Then, degree of dispersion (a mass average molecular weight/a number average molecular weight) of the obtained product was determined similar to the Example 1.

Subsequently, a black toner was manufactured using the obtained product and was evaluated in accordance with the aforementioned (a) toner manufacturing method and blow off charge performance evaluation method. Evaluation results are shown in Table 8.

TABLE 1

|  |  | Example 1 | Example 2 |
|---|---|---|---|
| Mononucleus phenolic compound (A) | p-t-butyl phenol (mol) | 0.45 | 0.35 |
| Multinucleus phenolic compound (B) | 2,2'-bis(4-hydroxy phenyl) propane (mol) | 0.032 | 0.05 |
| Aldehydes | paraformaldehyde (mol)* | 0.6 | 0.6 |
| Contents of multinucleus phenolic compound (B) in phenols (mol %) | | 6.6 | 12.5 |
| Mass average molecular weight | | 3300 | 3900 |
| Mass average molecular weight/number average molecular weight | | 1.8 | 2.2 |
| Blow-off charge performance evaluation | 5 minutes (μc/g) | −18.2 | −19.2 |
| | 1 hour (μc/g) | −27.1 | −27.9 |
| | 2 hours (μc/g) | −28.4 | −29.3 |
| | Charge rising ratio (%) | 67 | 69 |

*The value represents molar amount as formaldehyde.

TABLE 2

|  |  | Example 3 |
|---|---|---|
| Mononucleus phenolic compound (A) | p-t-butyl phenol (mol) | 0.45 |
| Multinucleus phenolic compound (B) | 2,2'-bis(4-hydroxy phenyl) propane (mol) | 0.032 |
| Aldehydes | paraformaldehyde (mol)* | 0.4 |
| | Furfural (mol) | 0.2 |
| Contents of multinucleus phenolic compound (B) in phenols (mol %) | | 6.6 |
| Mass average molecular weight | | 3,200 |
| Mass average molecular weight/number average molecular weight | | 1.9 |
| Blow-off charge performance evaluation | 5 minutes (μc/g) | −19.3 |
| | 1 hour (μc/g) | −28.9 |
| | 2 hours (μc/g) | −29.9 |
| | Charge rising ratio (%) | 67 |

*The value represents molar amount as formaldehyde.

TABLE 3

|  |  | Example 4 |
|---|---|---|
| Mononucleus phenolic compound (A) | p-t-butyl phenol (mol) | 0.225 |
| | p-t-octyl phenol (mol) | 0.225 |
| Multinucleus phenolic compound (B) | 2,2'-bis(4-hydroxy phenyl) propane (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 3,400 |
| Mass average molecular weight/number average molecular weight | | 1.9 |
| Blow-off charge performance evaluation | 5 minutes (μc/g) | −20.3 |
| | 1 hour (μc/g) | −28.9 |
| | 2 hours (μc/g) | −30.1 |
| | Charge rising ratio (%) | 70 |

*The value represents molar amount as formaldehyde.

TABLE 4

|  |  | Example 5 |
|---|---|---|
| Mononucleus phenolic compound (A) | p-t-butyl phenol (mol) | 0.34 |
| | 2-ethylhexyl 4-hydroxy benzoate (mol) | 0.11 |
| Multinucleus phenolic compound (B) | 2,2'-bis(4-hydroxy phenyl) propane (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 2,400 |
| Mass average molecular weight/number average molecular weight | | 1.9 |
| Blow-off charge performance evaluation | 5 minutes (μc/g) | −23.3 |
| | 1 hour (μc/g) | −32.9 |
| | 2 hours (μc/g) | −35.2 |
| | Charge rising ratio (%) | 71 |

*The value represents molar amount as formaldehyde.

TABLE 5

|  |  | Example 7 |
|---|---|---|
| Mononucleus phenolic compound (A) | p-t-butyl phenol (mol) | 0.45 |
| Multinucleus phenolic compound (B) | 1,1'-bis(4-hydroxy phenyl) cyclohexane (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 2,700 |
| Mass average molecular weight/number average molecular weight | | 1.8 |
| Blow-off charge performance evaluation | 5 minutes (μc/g) | −17.8 |
| | 1 hour (μc/g) | −26.3 |
| | 2 hours (μc/g) | −27.7 |
| | Charge rising ratio (%) | 68 |

*The value represents molar amount as formaldehyde.

TABLE 6

|  |  | Example 6 |
|---|---|---|
| Mononucleus phenolic compound (A) | p-t-butyl phenol (mol) | 0.34 |
| | 2-ethylhexyl 4-hydroxy benzoate (mol) | 0.11 |
| Multinucleus phenolic compound (B) | 4,4'-(1-phenylethylidene) bisphenol (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 2,700 |
| Mass average molecular weight/number average molecular weight | | 1.7 |
| Blow-off charge performance evaluation | 5 minutes (μc/g) | −23.8 |
| | 1 hour (μc/g) | −33.5 |
| | 2 hours (μc/g) | −35.8 |
| | Charge rising ratio (%) | 71 |

*The value represents molar amount as formaldehyde.

TABLE 7

|  |  | Example 8 |
|---|---|---|
| Mononucleus phenolic compound (A) | p-t-butyl phenol (mol) | 0.45 |
| Multinucleus phenolic compound (B) | 2,2'-bis(4-hydroxy phenyl) propane (mol) | 0.030 |
| | 4-4'-4''-ethylidine trisphenol | 0.005 |

TABLE 7-continued

|  |  | Example 8 |
|---|---|---|
| Aldehydes | paraformaldehyde (mol)* | 0.6 |
| Contents of multinucleus phenolic compound (B) in phenols (mol %) | | 7.6 |
| Mass average molecular weight | | 3,400 |
| Mass average molecular weight/number average molecular weight | | 2.1 |
| Blow-off charge performance evaluation | 5 minutes (μc/g) | −17.0 |
|  | 1 hour (μc/g) | −26.0 |
|  | 2 hours (μc/g) | −27.2 |
|  | Charge rising ratio (%) | 65 |

*The value represents molar amount as formaldehyde.

TABLE 8

|  |  | Example 9 | Comparative Example 1 | Comparative Example 3 |
|---|---|---|---|---|
| Mononucleus phenolic compound (A) | p-t-butyl phenol (mol) | 0.45 | 0.45 | 0.23 |
| Multinucleus phenolic compound (B) | Biphenol (mol) | 0.032 | 0.0032 | 0.110 |
| Aldehydes | paraformaldehyde (mol)* | 0.6 | 0.6 | 0.6 |
| Contents of multinucleus phenolic compound (B) in phenols (mol %) | | 6.6 | 0.71 | 32 |
| Mass average molecular weight | | 3,200 | 1,600 | 30,000 |
| Mass average molecular weight/number average molecular weight | | 1.9 | 1.1 | 22 |
| Blow-off charge performance evaluation | 5 minutes (μc/g) | −18.9 | −11.4 | −6.8 |
|  | 1 hour (μc/g) | −28.4 | −23.2 | −15.1 |
|  | 2 hours (μc/g) | −30.1 | −24.5 | −16.9 |
|  | Charge rising ratio (%) | 67 | 49 | 45 |

*The value represents molar amount as formaldehyde.

TABLE 9

|  |  | Example 10 |
|---|---|---|
| Mononucleus phenolic compound (A) | p-t-butyl phenol (mol) | 0.45 |
| Multinucleus phenolic compound (B) | 2,2'-bis(4-hydroxy phenyl) propane (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 3,300 |
| Mass average molecular weight/number average molecular weight | | 1.8 |
| Blow-off charge performance evaluation | 5 minutes (μc/g) | −17.9 |
|  | 1 hour (μc/g) | −26.8 |
|  | 2 hours (μc/g) | −28.9 |
|  | Charge rising ratio (%) | 67 |

*The value represents molar amount as formaldehyde.

TABLE 10

|  |  | Example 11 |
|---|---|---|
| Mononucleus phenolic compound (A) | p-t-butyl phenol (mol) | 0.35 |
|  | p-phenyl phenol (mol) | 0.10 |
| Multinucleus phenolic compound (B) | 2,2'-bis(4-hydroxy phenyl) propane (mol) | 0.032 |
| Aldehydes | paraformaldehyde (mol)* | 0.6 |

TABLE 10-continued

|  |  | Example 11 |
|---|---|---|
| Contents of multinucleus phenolic compound (B) in phenols (mol %) | | 6.6 |
| Mass average molecular weight | | 3,200 |
| Mass average molecular weight/number average molecular weight | | 1.9 |
| Blow-off charge performance evaluation | 5 minutes (μc/g) | −21.0 |
|  | 1 hour (μc/g) | −29.1 |
|  | 2 hours (μc/g) | −30.5 |
|  | Charge rising ratio (%) | 72 |

*The value represents molar amount as formaldehyde.

TABLE 11

|  |  | Example 12 |
|---|---|---|
| Mononucleus phenolic compound (A) | p-t-butyl phenol (mol) | 0.35 |
|  | p-(α-cumylphenol) (mol) | 0.10 |
| Multinucleus phenolic compound (B) | 2,2'-bis(4-hydroxy phenyl) propane (mol) | 0.032 |
| Aldehydes | paraformaldehyde (mol)* | 0.6 |
| Contents of multinucleus phenolic compound (B) in phenols (mol %) | | 6.6 |
| Mass average molecular weight | | 3,400 |
| Mass average molecular weight/number average molecular weight | | 1.9 |
| Blow-off charge performance evaluation | 5 minutes (μc/g) | −20.8 |
|  | 1 hour (μc/g) | −29.5 |
|  | 2 hours (μc/g) | −30.4 |
|  | Charge rising ratio (%) | 71 |

*The value represents molar amount as formaldehyde.

As it apparent from Tables 1 to 11, Comparative Example 1, wherein small amounts of multinucleus phenolic compound (B) was used, showed poor results of the blow-off charge performance evaluation such that charge amount after frictional charging for two hours was insufficient, and charge rising ratio in the initial stage was also poor. In Comparative Example 2, wherein excess amounts of multinucleus phenolic compound (B) was used, reaction had to be stopped, and therefore, product to be evaluated could not be obtained. Comparative Example 3, wherein a negative charge controlling agent was obtained by using dimethyl formaldehyde as a solvent which could dissolve the reaction product, showed poor results of the blow off charge performance evaluation such that charge amount after frictional charging for two hours was insufficient, and charge rising ratio in the initial stage was also poor.

The toner of Example 13, wherein it does not include colorant, was white, and therefore, it does not exert adverse effects on the color of toner, when it is used for color toner.

INDUSTRIAL APPLICABILITY

As explained above, a negative charge controlling agent of the present invention include a polycondensation material obtained by a condensation polymerization between aldehydes and phenols in which a specific mononucleus phenol compound (A) and a specific multinucleus phenol compound (B) are used together in a specific ratio, and therefore, charge rising ability of the agent is good, and the agent can provide sufficient charging ability to the toner. Moreover, since color of the negative charge controlling agent is pale white or pale yellow, the hue of toner is not influenced if the negative charge controlling agent is used for a color toner. Furthermore, compatibility between the agent and a binder resin is good, and dispersibility of the agent to the binder resin is also good. In this way, when the toner of the present invention wherein the negative charge controlling agent of the present invention is included are used, clear images can be obtained, and the agent is useful for electrophotography, electrostatic recording, and electrostatic printing.

The invention claimed is:

1. A toner for developing electrostatic charge images, wherein the toner comprises 0.1 to 10 parts by mass of a negative charge controlling agent per 100 parts by mass of a binder resin; and the negative charge controlling agent comprises polycondensation product obtained by polycondensation reaction of phenols and aldehydes, and the phenols comprise a (A) mononucleus phenolic compound which has one phenolic hydroxy group in which a hydrogen is bonded at the ortho position of a hydroxyl group of the phenolic hydroxy group; and a (B) multinucleus phenolic compound which has at least two phenolic hydroxy groups in which a hydrogen is bonded at the ortho position of a hydroxyl group of each of the at least two phenolic hydroxy groups of the (B) multinucleus phenolic compound; and the content of the (B) phenolic compound in the phenols is 1 to 30 mol %.

2. A toner according to claim 1, wherein the aldehyde is at least one of a paraformaldehyde and a formaldehyde; the (A) mononucleus phenolic compound is at least one kind selected from the group consisting of a p-alkyl phenol, a p-aralkyl phenol, a p-phenyl phenol, and a p-hydroxy benzoic acid ester; and the (B) multinucleus phenolic compound is bisphenols.

3. A toner according to claim 1, wherein a value of a mass average molecular weight/a number average molecular weight of the polycondensation product is 1.2 to 20.

* * * * *